United States Patent [19]

Randolph

[11] Patent Number: 4,844,394
[45] Date of Patent: Jul. 4, 1989

[54] BAKING SODA BOX HOLDER

[76] Inventor: Elizabeth Randolph, 600 Shore Acres Dr., Mamaroneck, N.Y. 10543

[21] Appl. No.: 185,673

[22] Filed: Apr. 25, 1988

[51] Int. Cl.$^4$ .............................................. A47B 96/06
[52] U.S. Cl. ................... 248/205.3; 211/88; 248/311.2
[58] Field of Search ............ 248/311.2, 205.3, 542, 248/146, 152, 205.4, 313; 211/88

[56] References Cited

U.S. PATENT DOCUMENTS

| | | | |
|---|---|---|---|
| 149,289 | 4/1874 | Bryan | 211/88 |
| 3,116,849 | 1/1964 | Brewer | 248/311.2 X |
| 3,168,275 | 2/1965 | Grondin | 248/311.2 X |
| 3,178,061 | 4/1965 | Giacalone | 248/311.2 X |
| 4,040,549 | 8/1977 | Sadler | 248/311.2 X |
| 4,482,123 | 11/1984 | Corbeil | 248/542 |
| 4,691,822 | 9/1987 | Malancon | 248/205.3 X |

*Primary Examiner*—J. Franklin Foss
*Attorney, Agent, or Firm*—Wolder, Gross & Yavner

[57] ABSTRACT

A baking soda box holder for use in confined spaces where odors linger, such as refrigerators or freezers. The holder is a rectangular cube and configuration with a solid bottom wall and at least one solid vertical wall. The remaining walls are defined by frames with open central areas. One of the vertical frames does not have bottom and top skirts to facilitate ingress and egress of the baking soda box. Two-sided adhesive tabs secure the unit in position, either to a wall via the solid vertical wall or a shelf via the solid bottom wall. Calendar strips may be secured to one of the exposed box walls to indicate when to replace the box.

10 Claims, 2 Drawing Sheets

BAKING SODA BOX HOLDER

BACKGROUND OF THE INVENTION

The present invention relates to baking soda box holders for use in confined spaces where odors linger, and more particularly, to a frame having at least one solid vertical wall and one solid bottom wall.

It is well known to place baking soda boxes in areas to remove odors. Normally, a standard box of baking soda is purchased and then the top is removed, and the open box is placed in an enclosed area such as a refrigerator box or a freezer box. It is known that after a certain period of time the efficacy of the baking soda diminishes considerably and a new box of baking soda must be inserted.

One of the major problems with baking soda is that, since it is an open box, if it is hit or if it tilts for any reason, it will spill and the baking soda will then fall out into an open area.

Yet another problem is to consider where to place the box. The box must be on a horizontal surface because that is the only place it can be put. Needless to say in refrigerators horizontal surface space is at a premium and that eliminates some of the cubic volume of the refrigerator.

OBJECTS AND ADVANTAGES OF THE PRESENT INVENTION

Accordingly, among the principal objects of the present invention is to provide a holder for a baking soda box.

Yet another object of the present invention is to provide a holder for a baking soda box which may be positioned on a vertical wall within an enclosure or on a horizontal wall within the enclosure.

Still yet another object of the present invention is to provide a device of the character described which will eliminate the problem of the baking soda box spilling or tipping over.

Yet another object of the present invention is to provide an improved box holder of the character described, which may be secured in a position, yet allows easy insertion and removal of baking soda boxes as is necessary.

Still yet a further object of the present invention is to provide a holder which may be easily and simply moved to different horizontal and vertical locations, as desired.

Still yet a further object of the present invention is to provide an improved baking soda box holder with open central areas and side walls in order to allow securement and observation of means to inform a user of the date when the box in question was opened and placed in position.

Accordingly, the above objects and advantages are realized by use of a rectangular, cubical configuration, having at least one solid vertical wall and at least one solid bottom wall. The remaining walls are formed of perpendicular skirts with large central open areas. At least one of the vertical walls has no horizontal skirts so that a baking soda box may be easily removed or inserted within position within the holder. Either of the solid walls are used to receive double-sided adhesive tabs so that with the vertical wall, the holder may be secured to a vertical wall of an enclosure. Similarly, with the horizontal solid wall, the holder may be secured to a horizontal surface.

Because of the large open areas, a dual sticking calendar strip may be secured to the box with the date of insertion so that the user knows when to remove the spent baking soda box from the holder.

The above description, as well as further objects and advantages of the present invention, will be more fully appreciated with reference to the following detailed description of a preferred, but nonetheless illustrative embodiment of the invention, when taken in conjunction with the following drawings, wherein.

DETAILED DESCRIPTION OF THE INVENTION

Figure 1:
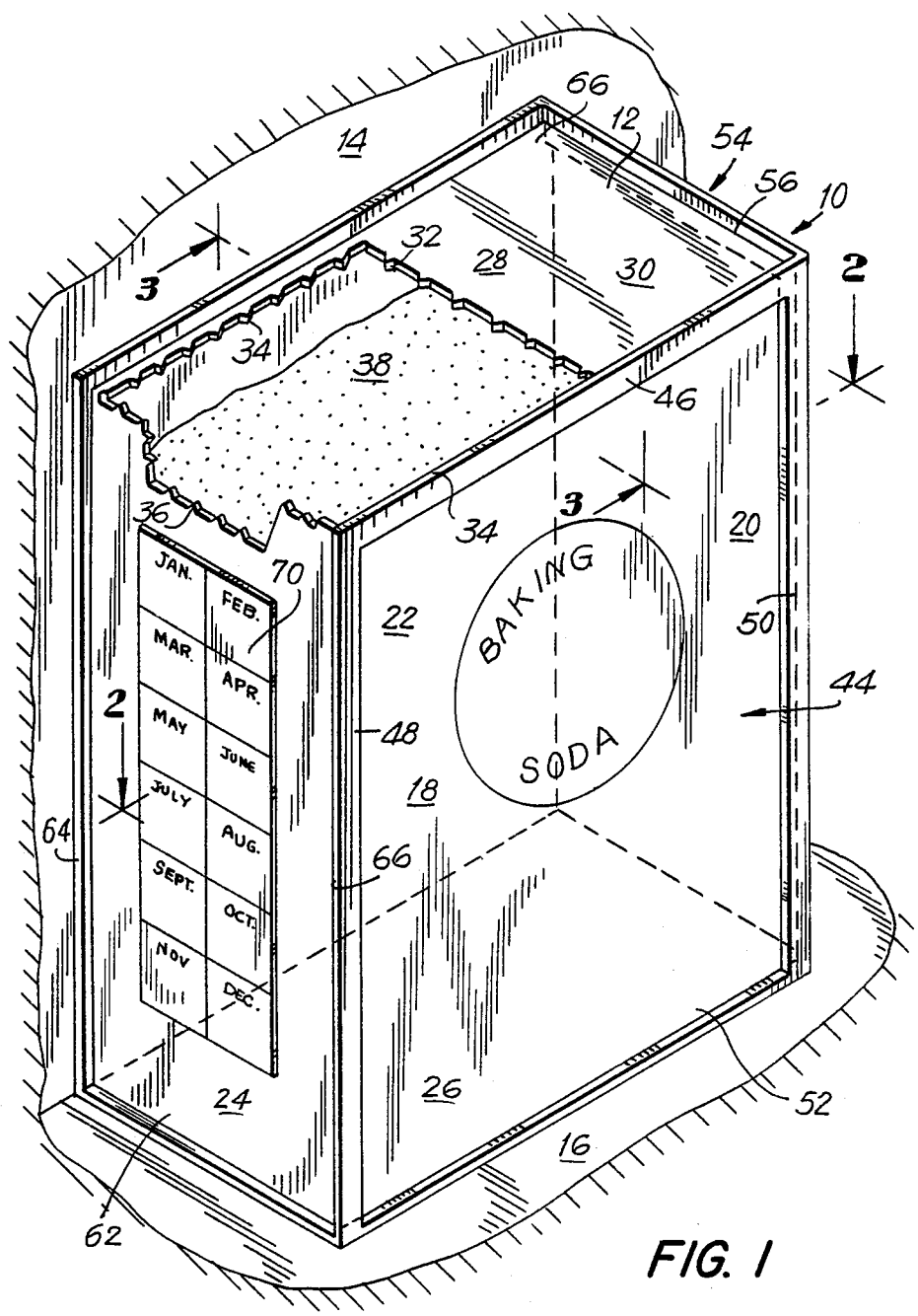
FIG. 1 is a front prospective view of my baking soda box holder with an open soda box in position and with a calendar strip located thereon.

Turning to FIG. 1, there is disclosed a baking soda box holder in accordance with my invention, which includes a holder 10 containing a standard size baking soda box 12, secured to either a vertical wall 14, or a horizontal wall 16 of an enclosure.

Turning more specifically to the baking soda box 12, it is a standard baking soda box such as might be a product of "Arm & Hammer" baking soda. The Arm & Hammer boxes come in standard 8 oz, 16 oz and 32 oz boxes. The 8 oz box is $3\frac{3}{4}$ inch high, $2\frac{7}{8}$ wide and $1\frac{1}{2}$ inch deep. The 16 oz box is $4\frac{5}{8}$ inch high, $3\frac{1}{2}$ inch wide and 2 inches deep, and the 32 oz box is $6\frac{3}{4}$ inch high, $4\frac{1}{2}$ inch wide and 2 inches deep. Thus, three different size holders would be necessary and helpful to accommodate the three different box sizes.

The box is defined in the usual fashion by a front wall 18, a right side wall 20, a rear wall 22 and a left side wall 24. Furthermore, there is a bottom wall 26 and a top wall 28, which consists of a permanent portion 30 and a removable portion not shown but defined by a striated side walls 32, 34 and 36. The box, of course, contains baking soda 38.

Figure 2:
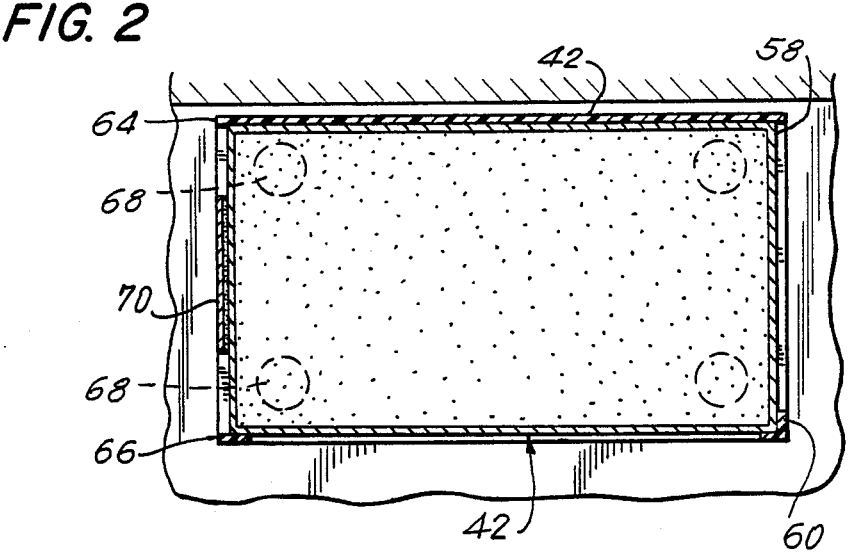
FIG. 2 is a plan sectional view taken along the line 2—2 of FIG. 1.
Figure 3:
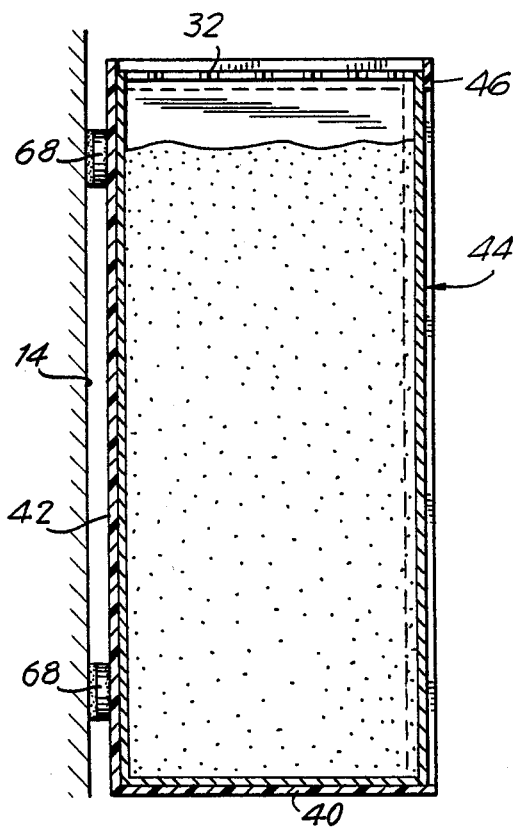
FIG. 3 is a vertical sectional view taken along the line 3—3 of FIG. 2.

The box 12 is secured within a frame 10 and the frame consists of a solid bottom wall 40 and a solid rear vertical wall 42. The frame is rectangular in cross section and is cubic in configuration. The remaining walls of the holder are defined by skirts. The front wall 44 is defined by an upper horizontal skirt 46, and optionally a bottom skirt (not shown). Since there are at least three skirts as will be described hereinafter, the bottom skirt is not necessary. The wall is also defined by a side skirts 48, 50 forming a frame with an open area 52. The front of the baking soda box is seen through this area. The right side wall 54 is similarly defined by an upper horizontal skirt 56 and side horizontal skirts 58, 60. Once again a bottom horizontal skirt is not shown since it is not necessary. Similarly, the top wall 62 is simply defined by the top edges of the wall 42 and the skirts 46, 56. Once again it is not necessary that there be skirts on the top wall. Finally, the left side wall 62 is defined by the left edges 64 of the walls 42 and the left edge 66 of the skirt 48. There is no bottom or top horizontal skirt on this wall. This is to allow simple ingress and egress of the soda box. As can be seen in FIGS. 2 and 3, double-sided adhesive tabs 68 may be secured to the side wall 42 and thence may be secured to the wall 14, which is the vertical side wall of enclosure. Alternatively, the tabs may be secured to the bottom wall 52 of the holder, which in turn may be secured to the bottom wall 16, a horizontal shelf. Thus, it is possible to mount this unit either up above the horizonal surface where it does not take up valuable horizontal shelf room, or it may be mounted on the horizontal shelf, if so desired. These two-way adhesive tabs are manufactured by Ross of Detroit, Mich., and bear the trademark "TACK-UPS". A calendar strip 70 may be used as seen in FIG. 1. An "X" may be placed in the month of insertion of the soda box within the holder. Furthermore, the date of insertion may also be placed within the month. Thus, the user can continuously see when the box was first placed in the enclosure, and at the desired time, the box may be replaced.

Thus, the box holder, which may come in three different sizes to accommodate the three standard sizes of soda box holders, may be made of a thin plastic frame with a typical thickness of perhaps ¼ inch, which would be sufficient to hold the box in place and be strong enough to retain it. The box of odor-absorbing baking soda may be placed anywhere where musty, bad smells accumulate without fear that the soda will spill or tip over. The baking soda will keep the air fresh and sweet smelling without any strong coverup aroma since baking soda absorbs all odors fast and leaves the surrounding atmosphere smelling fresh and clean.

The enclosure in which this unit may successfully be used are not only refrigerators and freezers, but dog houses and kennels, covered kitty liter trays, laundry hampers, a nursery room, a sick room, storage bins and closets, under-sink cabinets, clothes closets, basement work rooms, kitchen cupboards, lockers, and other such areas.

As can be seen, the present invention provides a significant advance over the state of the technology. As numerous additions, modifications and constructions can be performed within the scope of the invention, such scope is to be measured by the claims herein.

What is claimed:

1. A baking soda box holder for use within a confined space where odors linger, which comprises:
   (a) a box enclosure means sized to receive a baking soda box with at least two solid walls perpendicular to each other one of said walls being a bottom wall;
   (b) means to allow ingress and egress to the interior of the enclosure so as to insert and remove a box of baking soda, as desired; and
   (c) removable adhesive means secured to one of the two solid walls and either a side wall or a horizontal surface of the confined space; and
   (d) wherein the box enclosure includes frames for at least one of the other walls with at least an upper horizontal shirt defining an open area.

2. The invention according to claim 1, at least one of the vertical walls having no upper or lower horizontal skirts in order to allow easy ingress and egress of the baking soda box.

3. The invention according to claim 1, the frame further including left and side vertical skirts.

4. The invention according to claim 2, the vertical ingress and egress wall also having no vertical left and right skirt.

5. The invention according to claim 3, wherein there are provided at least one double-sided adhesive tabs secured to one of the solid walls in either a vertical wall or horizontal wall of the enclosure.

6. The invention according to claim 4, wherein there are provided at least one double-sided adhesive tabs secured to one of the solid walls in either a vertical wall or horizontal wall of the enclosure.

7. The invention according to claim 1, including calendar means which may be adhesively secured to one of the exposed surfaces of the soda box in order to indicate to the user the date that the box was opened and placed within the holder.

8. The invention according to claim 1, including calendar means which may be adhesively secured to one of the exposed surfaces of the soda box in order to indicate to the user the date that the box was opened and placed within the holder.

9. The invention according to claim 4, including calendar means which may be adhesively secured to one of the exposed surfaces of the soda box in order to indicate to the user the date that the box was opened and placed within the holder.

10. The invention according to claim 6, including calendar means which may be adhesively secured to one of the exposed surfaces of the soda box in order to indicate to the user the date that the box was opened and placed within the holder.

* * * * *